(12) United States Patent
Mire et al.

(10) Patent No.: US 11,957,385 B2
(45) Date of Patent: Apr. 16, 2024

(54) SPINAL IMPLANT SYSTEM AND METHOD

(71) Applicant: WARSAW ORTHOPEDIC INC., Warsaw, IN (US)

(72) Inventors: David A. Mire, Cordova, TN (US); Rodney R. Ballard, Lakeland, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 339 days.

(21) Appl. No.: 17/326,970

(22) Filed: May 21, 2021

(65) Prior Publication Data

US 2021/0275228 A1  Sep. 9, 2021

Related U.S. Application Data

(63) Continuation of application No. 15/812,858, filed on Nov. 14, 2017, now Pat. No. 11,051,854.

(51) Int. Cl.
*A61B 17/70* (2006.01)
*A61B 17/86* (2006.01)
*A61B 17/00* (2006.01)

(52) U.S. Cl.
CPC .......... *A61B 17/7014* (2013.01); *A61B 17/70* (2013.01); *A61B 17/7022* (2013.01); *A61B 17/7034* (2013.01); *A61B 17/7053* (2013.01); *A61B 17/8605* (2013.01); *A61B 2017/00004* (2013.01)

(58) Field of Classification Search
CPC . A61B 17/70; A61B 17/7014; A61B 17/7019; A61B 17/7022; A61B 17/7049; A61B 17/7053
USPC ................ 606/246, 257, 264–275, 278, 279
See application file for complete search history.

(56) References Cited

U.S. PATENT DOCUMENTS 6,514,255 B1 * 2/2003 Ferree ................ A61B 17/8861
606/76
2011/0245875 A1 * 10/2011 Karim ................ A61B 17/7037
606/264

* cited by examiner

*Primary Examiner* — Nicholas J Plionis
*Assistant Examiner* — Christina Negrellirodriguez
(74) *Attorney, Agent, or Firm* — Sorell, Lenna & Schmidt, LLP

(57) ABSTRACT

A method for treating a spine comprising the steps of: connecting at least one first fastener that defines an implant cavity with at least one vertebral level of a first portion of vertebrae; connecting at least one second fastener with at least one vertebral level of a second portion of the vertebrae; manipulating the vertebrae; manipulating a spinal rod to a selected configuration; connecting the spinal rod with the at least one first fastener such that the spinal rod is disposed at a selected position with the implant cavity; connecting a tether to a second fastener and the spinal rod; and reducing the spinal rod to a selected position relative to the second fastener with the tether. Systems, spinal constructs and surgical instruments are disclosed.

20 Claims, 5 Drawing Sheets

SPINAL IMPLANT SYSTEM AND METHOD

CROSS REFERENCE TO RELATED APPLICATIONS

This application is a continuation of U.S. patent application Ser. No. 15/812,858, filed Nov. 14, 2018, which is expressly incorporated by reference herein, in its entirety.

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. Correction treatments used for positioning and alignment may employ implants, such as vertebral rods, bone screws and sub-laminar wire for stabilization of a treated section of a spine. This disclosure describes an improvement over these prior technologies.

SUMMARY

In one embodiment, a method for treating a spine is provided. The method comprises the steps of: connecting at least one first fastener that defines an implant cavity with at least one vertebral level of a first portion of vertebrae; connecting at least one second fastener with at least one vertebral level of a second portion of the vertebrae; manipulating the vertebrae; manipulating a spinal rod to a selected configuration; connecting the spinal rod with the at least one first fastener such that the spinal rod is disposed at a selected position with the implant cavity; connecting a tether to a second fastener and the spinal rod; and reducing the spinal rod to a selected position relative to the second fastener with the tether. Systems, spinal constructs and surgical instruments are disclosed.

In one embodiment, the method comprises the steps of: connecting a first fastener that defines an implant cavity with a lower vertebral level of vertebrae; connecting a second fastener with an upper vertebral level of the vertebrae; manipulating the vertebrae; manipulating a spinal rod to a selected configuration; reducing the spinal rod to a completely reduced position with the implant cavity; and reducing the spinal rod to a selected position relative to a head of the second fastener.

In one embodiment, the method comprises the steps of: connecting a first fastener that defines an implant cavity with a lower vertebral level of vertebrae; connecting a second fastener with an upper vertebral level of the vertebrae; manipulating the vertebrae; manipulating a spinal rod to a selected configuration; reducing the spinal rod to a completely reduced position with the implant cavity; connecting a tether to the second fastener and the spinal rod; and reducing the spinal rod with the tether to a selected position relative to the second fastener.

BRIEF DESCRIPTION OF THE DRAWINGS

The present disclosure will become more readily apparent from the specific description accompanied by the following drawings, in which.

DETAILED DESCRIPTION

Figure 1:
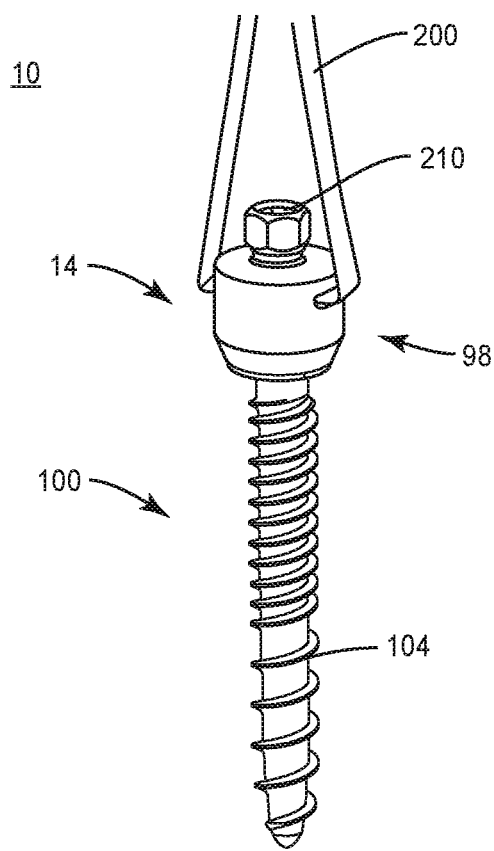
FIG. 1 is a perspective view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the present surgical system includes one or more spinal implants employed with a method of reducing a spinal rod to resist and/or prevent proximal junctional kyphosis (PJK), for example, on vertebral levels adjacent a posterior fixation construct. In some embodiments, the present surgical system includes an adjustable reduction device employed with a method to resist and/or prevent PJK, In some embodiments, the present surgical system is employed with a method of deformity correction that includes the steps of placing screws into vertebral bodies. In some embodiments, the method includes the steps of contouring a spinal rod to a desired shape of a spine and reducing the spinal rod into the screw heads to achieve desired correction. In some embodiments, the present surgical system achieves spinal re-alignment and avoids an incidence of PJK, for example, due to selective reduction of the spinal rod into upper instrumented vertebrae (UIV). In some embodiments, the present surgical system is employed with a method that stops reduction of the spinal rod before complete seating into the screw head as necessitated by the patient and anatomical considerations to potentially stave off the incidence of PJK. In some embodiments, this configuration provides the ability to not completely reduce the UIV and/or lower instrumented vertebrae (UV) to the spinal rod.

In some embodiments, the present surgical system includes one or more spinal implants and an adjustable reduction device employed with a method to resist and/or prevent PJK. In some embodiments, the present surgical system is employed with a method of deformity correction that includes the steps of placing screws into vertebral bodies; contouring a spinal rod to a desired shape of the spine; and reducing the spinal rod into the screw heads to achieve the desired correction. In some embodiments, the present surgical system is employed with a method of deformity correction that resists and/or prevents PJK and includes the steps of exposing and placing screws in tissue except for the UIV; and percutaneously or thru a mini-open incision placing UIV and/or UIV+1 bone anchors. In some embodiments, the bone anchor includes a screw that accepts a tether. In some embodiments, the method includes the step of conducting releases to loosen the spine for correction. In some embodiments, the method includes the step of contouring the spinal rod to the desired shape of the spine. In some embodiments, the method includes the step of reducing the spinal rod completely into all screws except at the UIV and/or UIV+1 levels. For example, at the UIV, the method includes the step of attaching a tether to and/or through the percutaneously placed screw and around the spinal rod. In some embodiments, the method includes the step of reducing the spinal rod to the tether/screw as required to achieve correction. In some embodiments, complete reduction is not required. In some embodiments, this configuration allows the UIV to not have the spinal rod completely reduced and allow flexibility in the system potentially reducing the incidence of PJK by lowering the reduction stresses at those levels. In some embodiments, the UIV can include UIV+1 and/or UIV+2. In some embodiments, this technique could also be utilized at the LIV and/or LIV+1 and/or LIV+2 to provide flexibility at the distal end of the construct.

In some embodiments, the present surgical system includes a spinal implant including a tether-based reduction screw. In some embodiments, the present surgical system is employed with deformity applications. In some embodiments, the present surgical system includes a tether-based reduction screw that enables an incomplete reduction of a vertebral body to a spinal rod. In some embodiments, the screw provides the ability to lock a dorsal height of a spinal construct at any point along a length of a tether.

In some embodiments, the present surgical system includes a spinal construct having a sublaminar tether connection to a spinal rod. In some embodiments, the present surgical system includes a spinal construct having a tether connection to a bone screw. In some embodiments, the spinal construct includes a set screw disposed at a bone screw head/shank interface to lock motion of a multi-axial screw head of the bone screw. In some embodiments, the set screw locks motion of a multi-axial screw head and fixates position of the tether relative to the bone screw.

In some embodiments, the present surgical system includes a spinal construct having a tether connection to a bone screw that employs a combination of high tension and locking at a rod/tether interface that fixates position of the tether relative to the bone screw.

In some embodiments, the present surgical system includes a spinal construct that allows for a direct connection between a flexible tether and a pedicle screw. In some embodiments, the spinal construct allows a secondary, independent connection of the tether to a spinal rod. In some embodiments, the spinal construct links the spinal rod and the bone screw through a tether braid. In some embodiments, the present surgical system includes a tensioning mechanism that reduces a vertebral body to a spinal rod. In some embodiments, the tensioning mechanism provides the ability to discontinue reduction at any point along a length of a tether. In some embodiments, the spinal construct includes an interface that can be fixated at a selected dorsal height relative to a vertebral body. In some embodiments, this configuration avoids potential weakening of the bone-screw interface and screw pull out.

In some embodiments, the present surgical system includes a spinal construct that is employed with a method including the steps of connecting a spinal construct having a tether to a bone screw. In some embodiments, the method includes the step of connecting the tether to a spinal rod. In some embodiments, the distance, for example, a dorsal height between the bone screw and the spinal rod, is adjustable. In some embodiments, the distance, for example, a dorsal height between the bone screw and the spinal rod, is lockable at a selected location along a tether length. In some embodiments, the present surgical system includes a device for reduction of the spinal construct that is adjustable and allows for incomplete and/or partial reduction.

In some embodiments, the present surgical system includes a spinal construct having a tether, a spinal rod and one or more bone fasteners, and a reduction mechanism. In some embodiments, the spinal rod can be reduced to spinal tissue in a range of reduction distance relative to the spinal tissue including engagement with the spinal tissue, partial or incomplete reduction and/or disposing the spinal rod at a selected dorsal height at any point along a length of a tether. In some embodiments, the present surgical system is employed for treating a large or hyperkyphosis or a spondylolisthesis reduction. In some embodiments, the present surgical system can be used for a translational correction technique. In some embodiments, the tether is used in a spondylolisthesis reduction to pull vertebrae towards the spinal rod.

In some embodiments, the present surgical system includes a pedicle screw, connectors and a spinal rod. In some embodiments, the pedicle screw includes a head for attachment to a tether, such as, for example, synthetic polyester fiber tape. In some embodiments, the pedicle screw includes a head having an anchor connected to the tether and being pivotable and/or rotatable in one or a plurality of axial directions relative to the pedicle screw. In some embodiments, the connector is engaged to the spinal rod and the tether to couple the spinal rod with the tether. In some embodiments, the connector locks the tether on the rod. In some embodiments, a tensioning device draws the spinal rod along the tether towards the pedicle screw.

In some embodiments, the surgical system includes a tether and a connector configured to fix a posterior spinal rod to a spine by the tether such that the spinal rod is fixed in a flexible and/or dynamic configuration. In some embodiments, the tether and the connector are fixed with a spine at an upper level of a spinal construct. In some embodiments, the spinal construct is fixed with a spine at one or a plurality of vertebral levels. In some embodiments, the tether is wrapped about a lamina, and the tether and the connector are fixed in position with a spinal rod. In some embodiments, the tether and the connector include one or a plurality of coupling members, such as, for example, set screws.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system, which includes components and/or implants of a spinal construct, surgical instruments and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 may be employed, for example, with minimally invasive procedures, including percutaneous techniques, mini-open surgical techniques and/or open surgical techniques to deliver and introduce surgical devices, surgical instrumentation and/or spinal implants at a surgical site within a body of a patient, which includes, for example, vertebrae. In some embodiments, the components of spinal implant system 10 are configured to deliver and introduce components of one or more spinal constructs 12 that include implants, such as, for example, one or more adaptors, tethers, receivers, spinal rods, bodies, sleeves, posts, connectors, plates and/or fasteners.

Spinal construct 12 forms one or more components of a surgical treatment implanted with tissue for positioning and alignment to stabilize a treated section of vertebrae. In some embodiments, spinal construct 12 provides one or more selectively coupled components and/or implants to facilitate large dorsal reduction, as described herein. In some embodiments, spinal construct 12 includes a bone screw 300 configured to receive a spinal rod 288 in a fully seated orientation and at least one bone fastener 98 configured for connection with a tether 200. This configuration allows a selective reduction and/or disposal of spinal rod 288 in a selected dorsal orientation relative to vertebral tissue and/or bone fastener 98, as described herein. In some embodiments, spinal rod 288 can be selectively reduced with bone screw 300.

In some embodiments, the components of spinal implant system 10 are employed to resist and/or prevent PJK by selectively positioning a spinal rod 288 with bone fastener 98, as described herein. For example, the components of spinal implant system 10 can be employed with spinal procedures on vertebral levels adjacent spinal construct 12, such as, for example, along vertebrae V. In some embodiments, spinal construct 12 includes a posterior fixation construct.

In assembly, operation and use, spinal implant system 10 is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal implant system 10 can be delivered or implanted as a pre-assembled device or can be assembled in situ. Spinal implant system 10 may be completely or partially revised, removed or replaced.

In use, to treat a selected section of vertebrae V, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder. An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region. Pilot holes are made in vertebrae V in a selected orientation.

Figure 3:
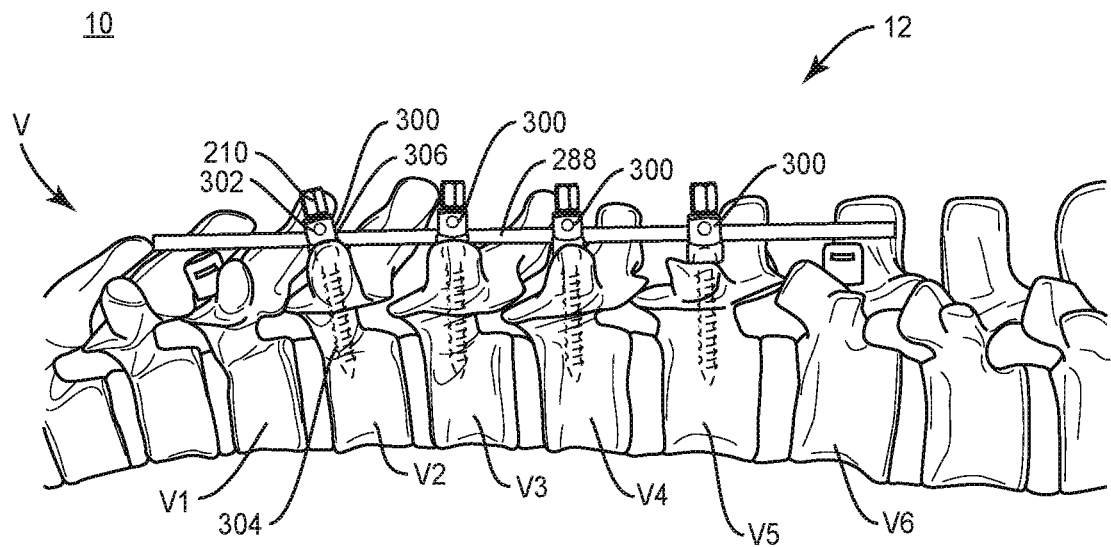
FIG. 3 is a side view of one embodiment of components of a surgical system in accordance with the principles of the present disclosure disposed with vertebrae.

Spinal construct 12 includes one or more bone screws 300, as shown in FIG. 3. Bone screw 300 includes a receiver 302 and a screw shaft 304. Receiver 302 includes an implant cavity 306 configured for disposal of spinal rod 288. Screw shaft 304 is configured to penetrate tissue. One or more bone screws 300 are aligned with selected pilot holes and fastened with the tissue of vertebrae V, such as, for example, vertebrae V2-V5. In some embodiments, bone screws 300 are disposed intermediate with spinal construct 12 and/or relative to UIV and LIV of vertebrae V.

Figure 4:
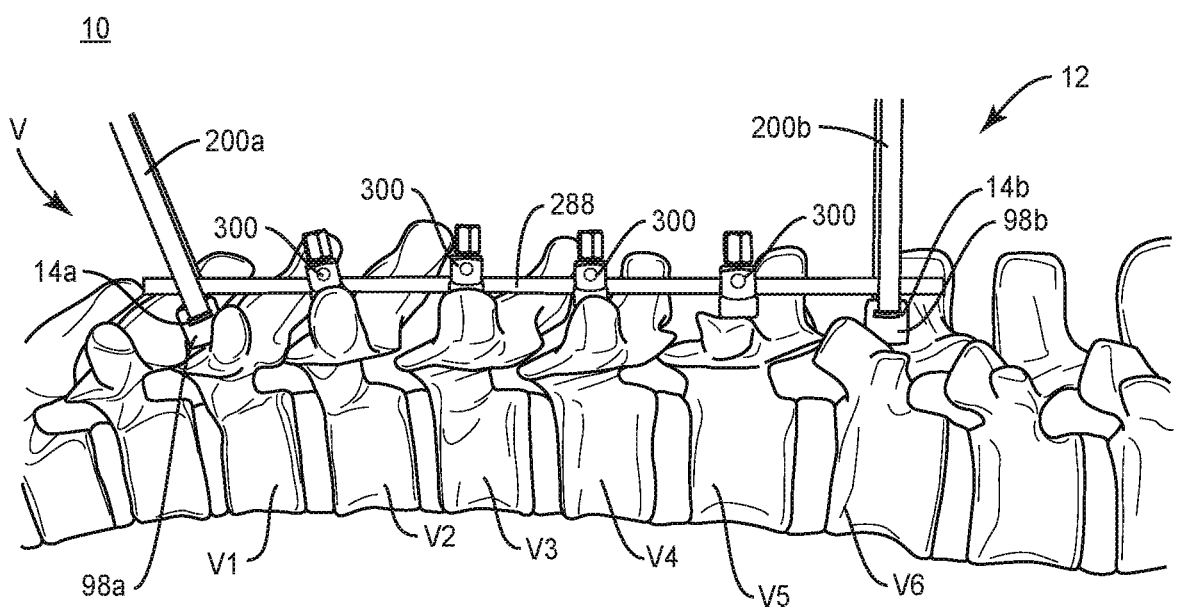
FIG. 4 is a side view of one embodiment of components of a surgical system in accordance with the principles of the present disclosure disposed with vertebrae.
Figure 5:
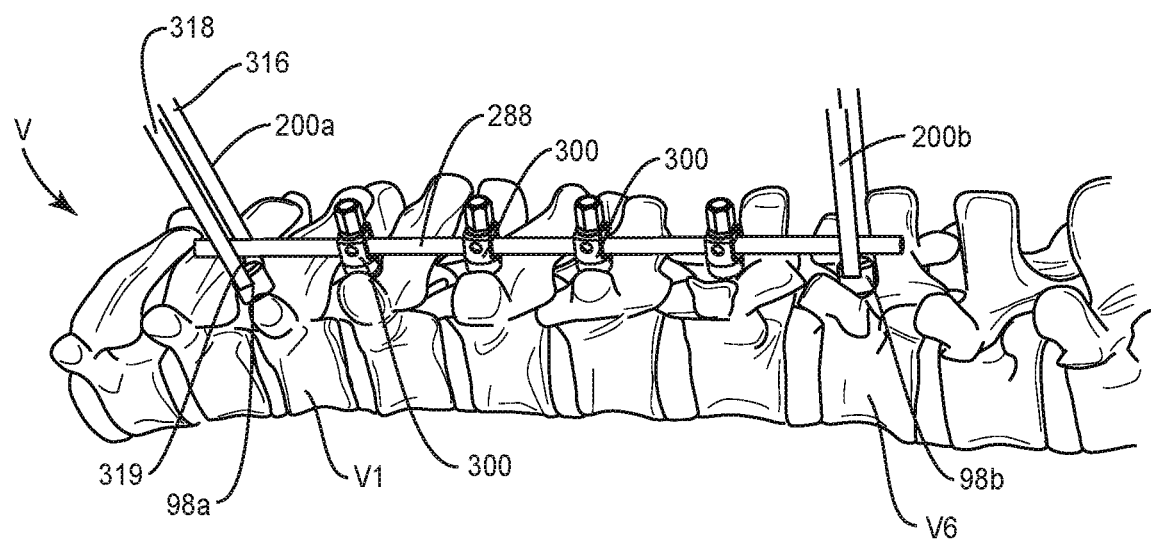
FIG. 5 is a perspective view of one embodiment of components of a surgical system in accordance with the principles of the present disclosure disposed with vertebrae.

Spinal construct 12 includes bone fasteners 98 configured for fixation with tissue of UIV including, for example, vertebra V1 and LIV including, for example, vertebra V6 of vertebrae V, as shown in FIGS. 4 and 5. Spinal rod 288 is selectively reduced with bone fasteners 98 to allow flexibility in spinal construct 12, for example, adjacent vertebrae V1, V6. In some embodiments, spinal rod 288 is selectively reduced with bone fasteners 98 to allow the UIV of vertebrae V and/or the LIV of vertebrae V to not have spinal rod 288 completely reduced, thereby resisting and/or preventing the incidence of PJK in vertebrae V by lowering reduction stresses from the components of spinal construct 12 at those vertebral levels associated with UIV and/or LIV. In some embodiments, UIV and/or LIV can include one or a plurality of vertebral levels.

Bone fasteners 98 include a bone screw 100 and a receiver 14. Receiver 14 is configured for disposal of tether 200, as described herein, and to provide a tether connection to bone screw 100, In some embodiments, receiver 14 employs tension and/or components to lock motion of bone screw 100 components and/or fixate position of tether 200 relative to bone screw 100, as described herein.

Figure 2:
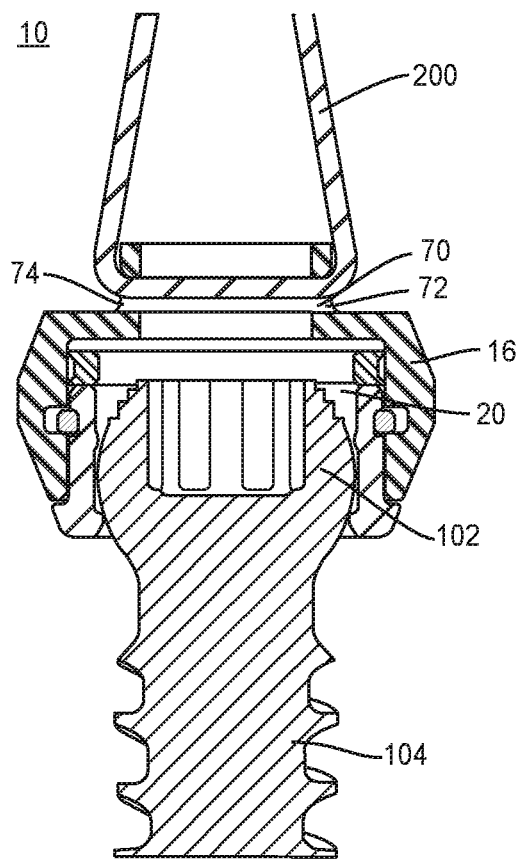
FIG. 2 is a break away cross section view of the components shown in FIG. 1.

Receiver 14 includes a wall 16, as shown in FIG. 2. Wall 16 includes an inner surface 18 that defines a cavity 20, Cavity 20 is configured for disposal of a head 102 of bone screw 100, as described herein. In some embodiments, receiver 14 is monolithically formed with head 102. In some embodiments, receiver 14 is manually engageable with head 102 in a non-instrumented assembly, as described herein. In some embodiments, manual engagement and/or non-instrumented assembly of receiver 14 and head 102 includes coupling without use of separate and/or independent instrumentation engaged with the components to effect assembly. In some embodiments, manual engagement and/or non-instrumented assembly includes a practitioner, surgeon and/or medical staff grasping receiver 14 and bone screw 100 and forcibly assembling, snap fitting, and/or pop fitting the components together. In some embodiments, a force in a range of 2-50 N is required to manually engage receiver 14 and bone screw 100 and forcibly assemble the components. In some embodiments, a force in a range of 5-10 N is required to manually engage receiver 14 and bone screw 100 and forcibly assemble the components.

In some embodiments, spinal implant system 10 comprises a spinal implant kit, which includes alternate receivers and/or screws. In some embodiments, receiver 14 is connected to a bone screw 100 to comprise a multi-axial, uni-axial, sagittally adjustable or fixed axis receiver/bone screw component of spinal construct 12.

Receiver 14 includes a surface 70 that defines a passageway 72. Passageway 72 is configured for disposal of tether 200 such that tether 200 can be fixed or translate through passageway 72 and relative to receiver 14 and/or bone screw 100 for tensioning and/or adjustment. Passageway 72 includes a transverse slot 74. Tether 200 is configured for disposal with passageway 72 such that tether 200 captures a portion of receiver 14, as described herein. Disposal and/or fixation of tether 200 with passageway 72 is employed to position spinal rod 288 in a selectively reduced orientation with bone screw 100 and/or at a selected dorsal orientation and/or distance relative to vertebrae V, as described herein. The dorsal height between vertebral tissue and/or bone screw 100, and spinal rod 288 can be adjusted and/or selectively fixed along tether 200. In some embodiments, the selected fixation includes an incomplete or partial reduction of spinal rod 288 relative to vertebral tissue, bone screws 300 and/or bone fasteners 98 along tether 200.

In some embodiments, receiver 14 includes an inner surface that includes a thread form (now shown). The thread form is configured for engagement with a set screw 210 such that set screw 210 is engaged with a surgical instrument to axially translate to engage tether 200 to selectively fix position and/or orientation of bone screw 100 relative to receiver 14, as described herein. In some embodiments, set screw 210 is configured to fix tether 200 relative to receiver 14 and/or bone screw 100. In some embodiments, set screw 210 may be fixed with receiver 14 in alternate fixation configurations, such as, for example, friction fit, pressure fit, locking protrusion/recess, locking keyway and/or adhesive.

Head 102 is connected with receiver 14 in a multi-axial configuration. Head 102 includes a tool engaging portion configured to engage a surgical tool or instrument, as described herein. Shaft 104 is configured to penetrate tissue, such as, for example, bone. In some embodiments, shaft 104 includes an outer surface having an external thread form. In some embodiments, the external thread form may include a single thread turn or a plurality of discrete threads.

Receiver 14 is pre-assembled with head 102. In some embodiments, receiver 14 can be assembled with bone screw 100 in-situ. For example, bone screw 100 is fastened with vertebrae V, as described herein, and receiver 14 is attached with head 102 in a non-instrumented assembly, as described herein. Bone screw 100 including receiver 14 is aligned with a pilot hole and fastened with the tissue of vertebrae V. Tether 200 is delivered along the surgical pathway to a surgical site adjacent receiver 14 and bone screw 100. Tether 200 is guided through passageway 72 for attachment with receiver 14 to capture receiver 14, as described herein.

Tether 200 extends between an end 316 and an end 318, as shown in FIG. 5. Tether 200 is configured for engagement with the components of spinal construct 12, as described herein. End 316 and end 318 form a loop 319 configured for disposal with passageway 72 of receiver 14, as described herein. Tensioning of tether 200 is configured to position spinal rod 288 in a selectively reduced orientation and/or disposes spinal rod 288 at a selected dorsal orientation and/or distance relative to vertebrae V, as shown in FIGS. 4 and 5. In some embodiments, the dorsal height between bone screw 100 and spinal rod 288 is selectively fixed along tether 200. In some embodiments, the selected fixation includes an incomplete or partial reduction of spinal rod 288 relative to vertebral tissue along tether 200. In some embodiments, spinal implant system 10 may include one or a plurality of tethers 200, each tether 200 being configured for disposal about a single and separate vertebral level. In some embodiments, a single vertebral level may include one or a plurality of tethers 200. In some embodiments, tether 200 is configured to apply a tension to receiver 14 to fix receiver 14 relative to bone screw 100, such as, for example, to resist and/or prevent multi-axial movement of receiver 14 relative to bone screw 100.

Tether 200 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, the flexibility of tether 200 includes movement in a lateral or side to side direction and prevents expanding and/or extension in an axial direction upon tensioning and attachment with receiver 14. In some embodiments, all or only a portion of tether 200 may have a semi-rigid, rigid or elastic configuration, and/or have elastic properties, similar to the material examples described herein, such that tether 200 provides a selective amount of expansion and/or extension in an axial direction. In some embodiments, tether 200 may be compressible in an axial direction. Tether 200 can include a plurality of separately attachable or connectable portions or sections, such as bands or loops, or may be monolithically formed as a single continuous element.

Tether 200 can have a uniform thickness/diameter. In some embodiments, tether 200 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 200 may be uniformly increasing or decreasing, or have alternate diameter dimensions along its length. In some embodiments, tether 200 may have various cross section configurations, such as, for example, oval, oblong, triangular, rectangular, square, polygonal, irregular, uniform, non-uniform, variable and/or tapered. In some embodiments, the surface of tether 200 may include engaging structures, such as, for example, barbs, raised elements and/or spikes to facilitate engagement with tissue of the targeted anatomy.

In some embodiments, the surface of tether 200 may include a pliable lead (not shown). In some embodiments, tether 200 may include a pliable lead such that tether 200 can be passed and/or guided through components of spinal construct 12 and/or cavities of spinal tissue to resist and/or prevent non-desirable and/or harmful engagement with selected and/or sensitive anatomy of the spinal tissue. In some embodiments, the pliable lead is soft and flexible and configured to pass through a sub-laminar cavity of vertebrae without adhering to dura matter of a spinal cord and/or surfaces of a lamina of a vertebral level. In some embodiments, all or only a portion of the pliable lead is fabricated from a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

In some embodiments, tether 200 may have various lengths. In some embodiments, tether 200 may be braided, such as a rope, or include a plurality of elongated elements to provide a predetermined force resistance. In some embodiments, tether 200 may be made from autograft and/or allograft, and be configured for resorbable or degradable applications. In one embodiment, tether 200 is a cadaver tendon. In one embodiment, tether 200 is a tendon that may be harvested, for example, from a patient or donor. In some embodiments, a tendon harvested from a patient may be affixed in remote locations with the patient's body.

Vertebrae V is manipulated to facilitate correction, alignment and/or release of vertebral levels for spinal treatment. Spinal rod 288 is selectively manipulated and contoured according to the spinal treatment parameters. Spinal rod 288 is connected with a surgical instrument, such as, for example, a rod reducer (not shown) for insertion and/or reduction with bone screws 300. Spinal rod 288 is reduced with bone screws 300, as shown in FIG. 3. Spinal rod 288 is reduced to a fully seated orientation with bone screws 300 to achieve desired correction. In some embodiments, spinal rod 288 may be selectively and/or partially reduced with bone screws 300, as described herein.

In some embodiments, a bone fastener 98*a* is aligned with a selected pilot hole in an UIV such as vertebra V1 and bone fastener 98*a* is fixed with vertebra V1. Tether 200*a* is connected with spinal rod 288 by wrapping tether 200*a* about spinal rod 288 and spinal rod 288 is translated along tether 200*a* to adjacent receiver 14*a*. As such, spinal rod 288 is intra-operatively reduced along tether 200*a* to bone fastener 98*a*.

Spinal rod 288 is reduced to a selected position adjacent receiver 14*a* and/or vertebrae V to conform to patient and anatomical considerations. For example, reduction of spinal rod 288 is selectively adjustable to provide flexibility to spinal construct 12 adjacent UIV such as vertebra V1 and, resist and/or prevent incidence of PJK, as described herein. In some embodiments, the selective reduction and/or positioning of spinal rod 288 along tether 200*a* relative to bone fastener 98*a* and/or vertebrae V includes an incomplete or partial reduction of spinal rod 288 relative to receiver 14*a* and/or vertebrae V.

A tensioner (not shown) is connected to tether 200*a*. The tensioner is actuated to tension tether 200*a* relative to bone fastener 98*a* and vertebra V1 attached therewith. The tensioner draws tether 200*a* to apply a tensioning force to tether 200*a* about vertebra V1 and tensions spinal construct 12 for attachment with vertebrae V and/or to apply corrective treatment to vertebrae V. In some embodiments, the tensioner includes a ratchet mechanism to selectively tension tether 200*a*. In some embodiments, the selected reduction and/or positioning of spinal rod 288 along tether 200*a* relative to bone fastener 98*a* and/or vertebrae V is fixed such that tether 200*a* is disposed in a locked orientation with spinal rod 288 and receiver 14*a*. In some embodiments, tether 200*a* is selectively fixed in position with spinal rod 288 and receiver 14*a* at a selected dorsal orientation and/or distance relative to vertebrae V. Selective reduction at the UIV provides flexibility in spinal construct 12 to resist and/or prevent incidence of PJK by lowering the reduction stresses from the components of spinal construct 12 at vertebra V1. In some embodiments, tether 200*a* can be fixed in position with spinal rod 288 and receiver 14*a* via manipulation, ties, tying, knotting, clips, clamps, connectors, fasteners, set screws and/or adhesive.

In some embodiments, a bone fastener 98*b* is aligned with a selected pilot hole in a LIV such as vertebra V6 and bone fastener 98*b* is fixed with vertebra V6. Tether 200*b* is connected with spinal rod 288 by wrapping tether 200*b* about spinal rod 288 and spinal rod 288 is translated along tether 200*b* to adjacent receiver 14*b*. As such, spinal rod 288 is intra-operatively reduced along tether 200*b* to bone fastener 98*b*.

Spinal rod 288 is reduced to a selected position adjacent receiver 14*b* and/or vertebrae V to conform to patient and anatomical considerations. For example, reduction of spinal rod 288 is selectively adjustable to provide flexibility to spinal construct 12 adjacent LIV such as vertebra V6 and, resist and/or prevent incidence of PJK, similar to that described herein with regard to spinal rod 288, tether 200*a* and bone fastener 98*a*. A tensioner is connected to tether 200*b* to tension tether 200*b* relative to bone fastener 98*b* and vertebra V6, similar to that described herein. The selected reduction and/or positioning of spinal rod 288 along tether 200*b* relative to bone fastener 98*b* and/or vertebrae V is fixed such that tether 200*b* is disposed in a locked orientation with spinal rod 288 and receiver 14*b*. Selective reduction at the LIV provides flexibility in spinal construct 12 to resist and/or prevent incidence of PJK by lowering the reduction stresses from the components of spinal construct 12 at vertebra V6. In some embodiments, tethers 200*b* can be fixed in position with spinal rod 288 and receiver 14*b* via manipulation, ties, tying, knotting, clips, clamps, connectors, fasteners, set screws and/or adhesive.

In some embodiments, spinal implant system 10 includes a second spinal rod 288 (not shown) delivered along the surgical pathway to the surgical site adjacent a contra-lateral side of vertebrae V. Second spinal rod 288 is connected with the contra-lateral side of vertebrae V via one or more bone screws 300, bone fasteners 98 and tethers 200, similar to that described herein. In some embodiments, first spinal rod 288 and second spinal rod 288 are fixed with vertebrae V in a side by side orientation and/or a bilateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal implant system 10 may be used to prevent or minimize curve progression in individuals of various ages.

Figure 6:
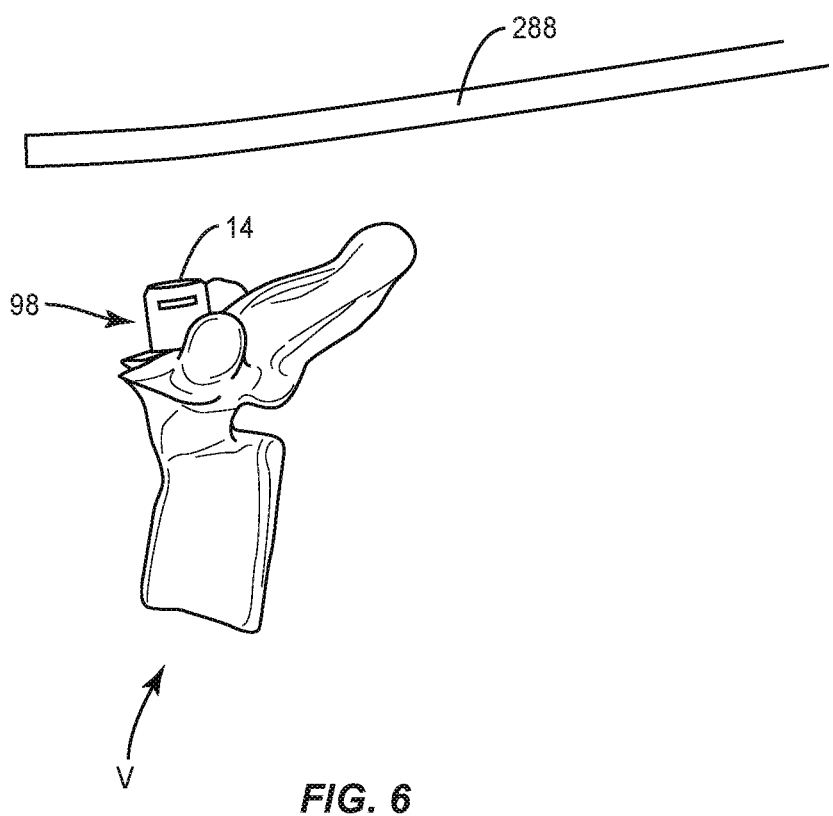
FIG. 6 is a side view of one embodiment of components of a surgical system in accordance with the principles of the present disclosure disposed with vertebrae.
Figure 7:
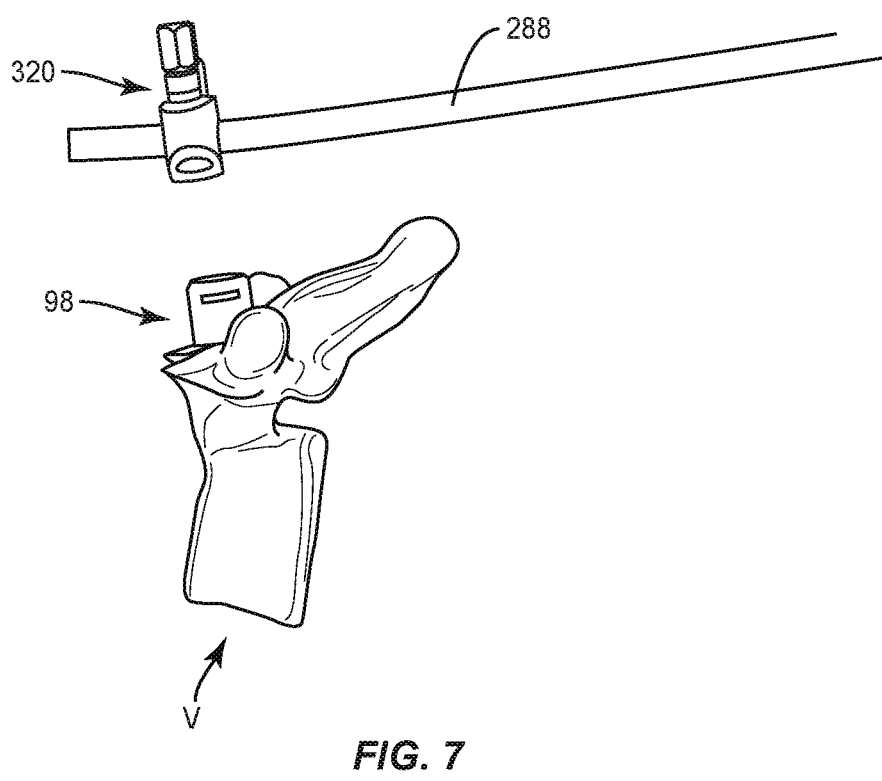
FIG. 7 is a side view of one embodiment of components of a surgical system in accordance with the principles of the present disclosure disposed with vertebrae.
Figure 8:
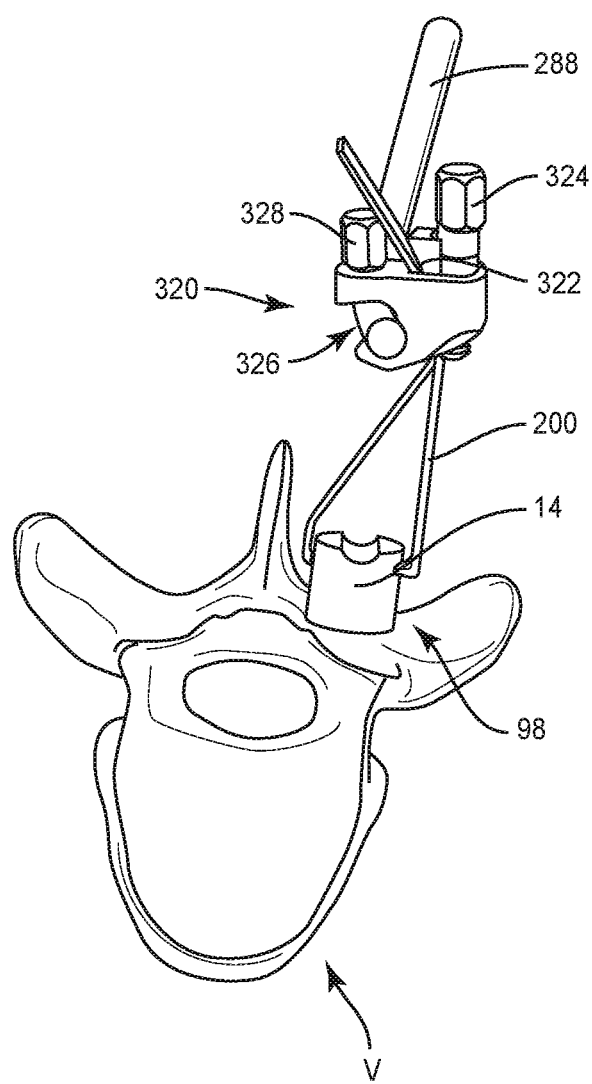
FIG. 8 is an axial view of one embodiment of components of a surgical system in accordance with the principles of the present disclosure disposed with vertebrae.

In one embodiment, as shown in FIGS. 6-8, spinal implant system 10, similar to the systems and methods described herein, includes spinal construct 12 having a connector 320 that connects spinal rod 288, tether 200 and bone fastener 98 for surgical treatment of vertebrae V, similar to that described herein. Tether 200 is delivered along the surgical pathway to a surgical site adjacent receiver 14 and bone fastener 98, similar to that described herein.

Tether 200 is guided through a passageway 322 of connector 320 for attachment with receiver 14. A set screw 324 is engageable with tether 200 between a locking and a non-locking orientation such that tether 200 is movable through connector 320. Spinal rod 288 is disposed with a bay 326 of connector 320 for attachment therewith. A set screw 328 is engageable with spinal rod 288 between a locking and a non-locking orientation such that spinal rod 288 is translatable relative to connector 320. Upon disposal of spinal rod 288 with connector 320 in a selected position, a surgical driver engages set screw 328 to fix position of spinal rod 288 with connector 320 for reduction of spinal rod 288 relative to bone screw 98 and vertebrae V via tether 200.

Connector 320 having spinal rod 288 disposed therewith is reduced along tether 200 to a selected position adjacent receiver 14 and/or vertebrae V to provide flexibility to spinal construct 12 adjacent an UIV and/or a LIV of vertebrae V to resist and/or prevent incidence of PJK, similar to that described herein. In some embodiments, the selective reduction and/or positioning of connector 320 along tether 200 relative to bone fastener 98 and/or vertebrae V includes an incomplete or partial reduction of spinal rod 288 relative to receiver 14 and/or vertebrae V, similar to that described herein.

A tensioner (not shown) is connected to connector 320 to tension tether 200 relative to bone fastener 98 and vertebrae V attached therewith, similar to that described herein. In some embodiments, connector 320 is selectively fixed in position with spinal rod 288 and receiver 14 at a selected dorsal orientation and/or distance relative to vertebrae V. Selective reduction at an UIV and/or a LIV of vertebrae V provides flexibility in spinal construct 12 to resist and/or prevent incidence of PJK by lowering the reduction stresses from the components of spinal construct 12 adjacent an UIV and/or a LIV of vertebrae V. Set screw 324 engages tether 200 in a locking configuration to fix position of tether 200 relative to receiver 14 and/or bone fastener 98, such that connector 320 having spinal rod 288 disposed therewith is reduced to a selected position and fixed relative to receiver 14 and/or vertebrae V for surgical treatment of vertebrae V, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method comprising:
   providing a first fastener having opposite proximal and distal ends;
   threading the distal end into a first vertebra;
   threading a second fastener into a second vertebrae;
   engaging a spinal rod with the first fastener;
   positioning a tether having opposite first and second ends such that the tether extends about the spinal rod and through the second fastener, the tether being positioned such that the first and second ends are proximal to the proximal end; and
   translating the spinal rod along the tether toward the second fastener.

2. The method recited in claim 1, wherein engaging the spinal rod with the first fastener comprises reducing the spinal rod into an implant cavity of the first fastener.

3. The method recited in claim 1, wherein engaging the spinal rod with the first fastener comprises reducing the spinal rod into an implant cavity of the first fastener to a fully reduced position with the implant cavity and reducing the spinal rod to a selected position relative to a head of the second fastener.

4. The method recited in claim 1, further comprising manipulating the vertebrae subsequent to threading the fasteners into the vertebrae and prior to engaging the spinal rod with the first fastener.

5. The method recited in claim 1, further comprising manipulating the spinal rod to a selected configuration prior to engaging the spinal rod with the first fastener.

6. The method recited in claim 1, wherein positioning the tether such that the tether extends about the spinal rod and through the second fastener comprises wrapping the tether about the spinal rod.

7. The method recited in claim 1, wherein the tether is spaced apart from the vertebrae when the tether extends about the spinal rod and through the second fastener.

8. The method recited in claim 1, wherein translating the spinal rod along the tether toward the second fastener comprises reducing the spinal rod to a selected position relative to the second fastener.

9. The method recited in claim 1, wherein:
   threading the first fastener into the first vertebra includes a percutaneous surgical procedure; and
   threading the second fastener into the second vertebrae includes an open surgical procedure.

10. The method recited in claim 1, wherein the second fastener includes a head defining a slot configured for disposal of the tether.

11. A method comprising:
    providing a first fastener having opposite proximal and distal ends;
    threading the distal end into a first vertebra;
    threading a second fastener into a second vertebrae;
    reducing a spinal rod into an implant cavity of the first fastener;
    positioning a tether having opposite first and second ends such that the tether is wrapped about the spinal rod, the tether extends through a passageway of the second fastener and the tether is spaced apart from the vertebrae, the tether being positioned such that the first and second ends are proximal to the proximal end; and
    reducing the spinal rod by translating the spinal rod along the tether toward the second fastener.

12. The method recited in claim 11, wherein reducing the spinal rod into the implant cavity comprises reducing the spinal rod to a fully reduced position with the implant cavity and reducing the spinal rod to a selected position relative to a head of the second fastener.

13. The method recited in claim 11, further comprising manipulating the vertebrae subsequent to threading the fasteners into the vertebrae and prior to engaging the spinal rod with the first fastener.

14. The method recited in claim 11, further comprising manipulating the spinal rod to a selected configuration prior to reducing the spinal rod into the implant cavity.

15. The method recited in claim 11, wherein:
threading the first fastener into the first vertebra includes a percutaneous surgical procedure; and
threading the second fastener into the second vertebrae includes an open surgical procedure.

16. The method recited in claim 11, wherein the second fastener includes a head defining the passageway.

17. The method recited in claim 11, wherein:
the second fastener includes spaced apart openings in communication with the passageway; and
positioning the tether such that the tether extends through the passageway comprises positioning the tether such that ends of the tether extend through the openings.

18. The method recited in claim 11, wherein the tether has a flexible configuration.

19. The method recited in claim 11, wherein the fasteners each include a threaded shaft and a receiver that is rotatable relative to the shaft.

20. A method comprising:
providing a first fastener having opposite proximal and distal ends;
threading the distal end into a first vertebra;
threading a second fastener into a second vertebrae;
reducing a spinal rod into an implant cavity of the first fastener;
positioning a tether having opposite first and second ends such that the tether is wrapped around the spinal rod, the tether extends through a passageway of the second fastener and the tether is spaced apart from the vertebrae, the tether being positioned such that the first and second ends are proximal to the proximal end;
reducing the spinal rod by translating the spinal rod along the tether toward the second fastener; and
threading a set screw into the second fastener such that the set screw engages the tether to fix a portion of the tether relative to the second fastener.

* * * * *